(12) United States Patent
Welch

(10) Patent No.: US 7,011,671 B2
(45) Date of Patent: Mar. 14, 2006

(54) CARDIAC IMPLANT DEVICE TETHER SYSTEM AND METHOD

(75) Inventor: Jeffrey Welch, New Hope, MN (US)

(73) Assignee: Atritech, Inc., Plymouth, MN (US)

( * ) Notice: Subject to any disclaimer, the term of this patent is extended or adjusted under 35 U.S.C. 154(b) by 397 days.

(21) Appl. No.: 10/198,261

(22) Filed: Jul. 16, 2002

(65) Prior Publication Data

US 2003/0023262 A1 Jan. 30, 2003

Related U.S. Application Data

(60) Provisional application No. 60/306,178, filed on Jul. 18, 2001.

(51) Int. Cl.
*A61M 29/00* (2006.01)

(52) U.S. Cl. .................. 606/194; 606/195; 606/198; 606/200

(58) Field of Classification Search ................ 606/194, 606/195, 198, 108, 191, 200, 1, 151; 623/1.1, 623/11.11; 604/104
See application file for complete search history.

(56) References Cited

U.S. PATENT DOCUMENTS

| | | |
|---|---|---|
| 178,283 A | 6/1876 | French |
| 1,967,318 A | 7/1934 | Monahan |
| 3,844,302 A | 10/1974 | Klein |
| 3,874,388 A | 4/1975 | King et al. |
| 4,007,743 A | 2/1977 | Blake |

(Continued)

FOREIGN PATENT DOCUMENTS

| | | |
|---|---|---|
| WO | WO 93/13712 | 7/1993 |
| WO | WO 97/21402 | 6/1997 |
| WO | WO 97/28749 | 8/1997 |
| WO | WO 98/02100 | 1/1998 |
| WO | WO 98/17187 | 4/1998 |

(Continued)

OTHER PUBLICATIONS

Cragg et al., "Nonsurgical Placement of Arterial Endoprosthesis: A New Technique Using Nitinol Wire," *Radiology* vol. 147, No. 1, pp. 261–263, Apr. 1983.
Cragg, et al., "A New Percutaneous Vena Cava Filter", *ALJ*, 141: 601–604, Sep. 1983.
Sugita et al., "Nonsurgical Implantation of a Vascular Ring Prosthesis Using Thermal Shape Memory Ti/Ni Alloy (Nitinol Wire), " *Trans. Am. Soc. Artif. Intern. Organs*, vol. XXXII, 30–34, 1986.
Ruttenberg, "Nonsurgical Therapy of Cardiac Disorders," *Pediatric Consult*, vol. 5, No. 2, pages not numbered, 1986.
Rashkind et al., "Nonsurgical Closure of patent ductus arteriosus: clinical application of the Rashkind PDA Occluder System," *Circulation* 75, No. 3, 583–592, 1987.
Lock et al., "Transcatheter Umbrella Closure of Congenital Heart Defects," *Circulation*, vol. 75, No. 3, 593–599, 1987.
Wessel, et al. "Outpatient Closure of the patent ductus arteriosus," *Circulation*, vol. 77, No. 5, 1068–1071, 1988.
Lock et al., "Transcatheter Closure of Atrial Septal Defects," *Circulation*, vol. 79, No. 5, 1091–1099, May 1989.

Primary Examiner—Glenn K. Dawson
Assistant Examiner—Michael G. Mendoza
(74) Attorney, Agent, or Firm—Fish & Neave IP Group Ropes & Gray LLP

(57) ABSTRACT

Catheterization apparatus for implanting devices is provided with a device tether. The apparatus includes a device delivery tube that provides a pathway for moving implant devices through a patient's vasculature to internal body cavities. The implant devices are carried or pushed through the device delivery tube by a tubular push rod. The implant devices are tethered to a line passing through the push rod lumen. After deployment, the implant devices may be retracted into the device delivery tube for repositioning or retrieval by pulling on the tether.

2 Claims, 2 Drawing Sheets

U.S. PATENT DOCUMENTS

| | | |
|---|---|---|
| 4,341,218 A | 7/1982 | Ü |
| 4,585,000 A | 4/1986 | Hershenson |
| 4,603,693 A | 8/1986 | Conta et al. |
| 4,665,906 A | 5/1987 | Jervis |
| 4,710,192 A | 12/1987 | Liotta et al. |
| 4,917,089 A | 4/1990 | Sideris |
| 4,921,484 A | 5/1990 | Hillstead |
| 5,037,810 A | 8/1991 | Sabila, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,078,736 A | 1/1992 | Behl |
| 5,108,420 A | 4/1992 | Marks |
| 5,171,259 A | 12/1992 | Inoue |
| 5,176,692 A | 1/1993 | Wilk et al. |
| 5,192,301 A | 3/1993 | Kamiya et al. |
| 5,256,146 A | 10/1993 | Ensminger et al. |
| 5,258,042 A | 11/1993 | Mehta |
| 5,284,488 A | 2/1994 | Sideris |
| 5,306,234 A | 4/1994 | Johnson |
| 5,334,217 A | 8/1994 | Das |
| 5,350,399 A | 9/1994 | Erlebacher et al. |
| 5,353,784 A | 10/1994 | Nady-Mohamed |
| 5,370,657 A | 12/1994 | Irie |
| 5,375,612 A | 12/1994 | Cottenceau et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,702,421 A | 12/1997 | Schneidt |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,810,874 A | 9/1998 | Lefebvre |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,846,260 A | 12/1998 | Maahs |
| 5,846,261 A | 12/1998 | Kotula et al. |
| 5,849,005 A | 12/1998 | Garrison et al. |
| 5,851,232 A | 12/1998 | Lois |
| 5,855,597 A | 1/1999 | Jayaraman |
| 5,865,791 A | 2/1999 | Whayne et al. |
| 5,865,802 A | 2/1999 | Yoon et al. |
| 5,868,708 A | 2/1999 | Hart et al. |
| 5,876,367 A | 3/1999 | Kaganov et al. |
| 5,882,340 A | 3/1999 | Yoon |
| 5,885,258 A | 3/1999 | Sachdeva et al. |
| 5,895,399 A | 4/1999 | Barbut et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,954,694 A | 9/1999 | Sunseri |
| 5,957,940 A | 9/1999 | Tanner et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,068,621 A | 5/2000 | Balceta et al. |
| 6,074,357 A | 6/2000 | Kaganov et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,132,438 A | 10/2000 | Fleischman et al. |
| 6,136,016 A | 10/2000 | Barbut et al. |
| 6,139,527 A | 10/2000 | Laufer et al. |
| 6,152,144 A | 11/2000 | Lesh et al. |
| 6,161,543 A | 12/2000 | Cox et al. |
| 6,231,561 B1 | 5/2001 | Frazier et al. |
| 6,231,589 B1 | 5/2001 | Wessman et al. |
| 6,235,045 B1 * | 5/2001 | Barbut et al. ............... 606/200 |
| 6,364,895 B1 * | 4/2002 | Greenhalgh ................. 606/200 |
| 6,371,971 B1 * | 4/2002 | Tsugita et al. .............. 606/200 |
| 6,551,303 B1 | 4/2003 | Van Tassel et al. |
| 6,652,555 B1 | 11/2003 | Van Tassel et al. |
| 6,652,556 B1 | 11/2003 | Van Tassel et al. |
| 6,689,150 B1 | 2/2004 | Van Tassel et al. |
| 2002/0022860 A1 | 2/2002 | Borillo et al. |
| 2002/0035374 A1 | 3/2002 | Borillo et al. |
| 2003/0057156 A1 | 3/2003 | Peterson et al. |

FOREIGN PATENT DOCUMENTS

| | | |
|---|---|---|
| WO | WO 98/23322 | 6/1998 |
| WO | WO 99/07289 | 2/1999 |
| WO | WO 99/08607 | 2/1999 |
| WO | WO 99/30640 | 6/1999 |
| WO | WO 00/27292 | 5/2000 |
| WO | WO 00/53120 | 9/2000 |
| WO | WO 01/21247 | 3/2001 |
| WO | WO 01/26726 | 4/2001 |
| WO | WO 01/30266 | 5/2001 |

* cited by examiner

CARDIAC IMPLANT DEVICE TETHER SYSTEM AND METHOD

This application claims the benefit of U.S. provisional application No. 60/306,178, filed Jul. 18, 2001, which is hereby incorporated by reference in its entirety herein.

BACKGROUND OF THE INVENTION

1. Field of the Invention

The invention relates to apparatus for implanting devices in atrial appendages. The implanted devices may be used to filter or otherwise modify blood flow between the atrial appendage and an associated atrium of the heart to prevent thrombi from escaping from the atrial appendage into the body's blood circulation system. In particular the invention relates to apparatus for percutaneous delivery and implantation of such devices.

2. Description of the Related Art

There are a number of heart diseases (e.g., coronary artery disease, mitral valve disease) that have various adverse effects on a patient's heart. An adverse effect of certain cardiac diseases, such as mitral valve disease, is atrial (or auricular) fibrillation. Atrial fibrillation leads to depressed cardiac output. A high incidence of thromboembolic (i.e., blood clot particulate) phenomena is associated with atrial fibrillation, and the left atrial appendage (LAA) is frequently the source of the emboli (particulates).

Thrombi (i.e., blood clots) formation in the LAA may be due to stasis within the fibrillating and inadequately emptying LAA. Blood pooling in the atrial appendage is conducive to the formation of blood clots. Blood clots may accumulate, and build upon themselves. Small or large fragments of the blood clots may break off and propagate out from the atrial appendage into the atrium. The blood clot fragments can then enter the body's blood circulation and embolize distally into the blood stream.

Serious medical problems result from the migration of blood clot fragments from the atrial appendage into the body's blood stream. Blood from the left atrium and ventricle circulates to the heart muscle, the brain, and other body organs, supplying them with necessary oxygen and other nutrients. Emboli generated by blood clots formed in the left atrial appendage may block the arteries through which blood flows to a body organ. The blockage deprives the organ tissues of their normal blood flow and oxygen supply (ischemia), and depending on the body organ involved leads to ischemic events such as heart attacks (heart muscle ischemia) and strokes (brain tissue ischemia).

It is therefore important to find a means of preventing blood clots from forming in the left atrial appendage. It is also important to find a means to prevent fragments or emboli generated by any blood clots that may have formed in the atrial appendages, from propagating through the blood stream to the heart muscle, brain or other body organs.

Some recently proposed methods of treatment are directed toward implanting a plug-type device in an atrial appendage to occlude the flow of blood therefrom.

Another treatment method for avoiding thromboembolic events (e.g., heart attacks, strokes, and other ischemic events) involves filtering out harmful emboli from the blood flowing out of atrial appendages. Co-pending and co-owned U.S. patent application Ser. No. 09/428,008 now U.S. Pat. No. 6,551,303; U.S. patent application Ser. No. 09/614,091, U.S. now U.S. Pat. No. 6,689,150; U.S. patent application Ser. No. 09/642,291, now U.S. Pat. No. 6,652,555; U.S. patent application Ser. No. 09/697,628, now U.S. Pat. No. 6,652,556; U.S. patent application Ser. No. 09/932,512, now published as U.S. Application No. 20020022860A1; U.S. patent application Ser. No. 09/960,749, now published as U.S. Application Publication No. 20020035374A1; and U.S. patent application Ser. No. 10/094,730, now published U.S. Application Publication No. 20030057156A1, all of which are hereby incorporated by reference in their entireties herein, describe filtering devices which may be implanted in an atrial appendage to filter the blood flow therefrom.

Common catheterization methods (including transseptal procedures) may be used to implant the devices in the atrial appendages. A narrow diameter catheter delivery tube is passed through the patient's vasculature to provide a conduit or pathway to the patient's atrial appendage. The implant devices generally have an elastic or compressible structure. This structure allows a device to be reversibly compacted to a small size that is suitable for insertion in the narrow diameter catheter delivery tube. A compacted device is attached to a guide wire or a push rod, and moved through the catheter delivery tube to a deployment position within the patient's heart cavity. Then by remote manipulation, the compacted device may be expanded in situ, and detached from the push rod or guide wire to serve as an atrial appendage implant.

The success of the atrial implant treatment procedure depends on the deployment of the implant device in an appropriate position and orientation (relative to the atrial appendage). To be effective the device must intercept all of the blood flow through the atrial appendage. For example, for a filter device implant to be successful, the device should be positioned and oriented so that all of the atrial appendage blood flow is directed through device filter elements, and so that there is no seepage around the device.

However, the percutaneous catheterization delivery techniques used for implant delivery (which often rely on operator dexterity) may not be sufficiently precise to place the device in a desirable orientation at the first attempt. Inadvertent movement or instability in the position or orientation of the device delivery catheter tube may make precise placement of an atrial appendage implant device difficult. Placing a device in a suitable deployment position with a desirable orientation may in some cases require repeated position probing or adjustment. Further, properly placed compacted devices, may during subsequent in situ expansion or detachment become dislodged or misoriented. Under some conditions, it may even be desirable to withdraw a delivered device.

Co-pending and co-owned U.S. patent application Ser. No. 09/932,512 describes a catheterization apparatus having a positioning device or guide, which enables position probing and readjustment of as-delivered implant device positions. Consideration is now being given to additional catheterization apparatus features to enable controlled recovery or repositioning of implanted devices.

SUMMARY OF THE INVENTION

The invention provides a catheterization apparatus having a system by which implant devices are attached to a tether during device delivery and deployment. The catheterization apparatus includes a delivery tube that provides a conduit or a pathway for moving implant devices through a patient's vasculature to internal body cavities. The implant devices may be moved through the delivery tube, and expelled or released from the distal end of the delivery tube for deployment in the internal body cavities. Conventional mechanisms such as a tubular push rod or shaft may be used to move a device through the catheter delivery tube.

The tether system provides remote mechanical control over implant devices, which are expelled or released from the distal end of a catheter delivery tube into the internal body cavities of a patient. This mechanical control over post deployment devices enables a physician to recover and reposition implant devices as needed.

In one embodiment of the invention, the tether system includes a wire-dispensing hub connected to the device push rod or shaft. The tether system may be used with implant devices that have (or those that can be fitted with a suitable wire-connection feature, for example, an eye hole. A flexible wire (or line) is dispensed by the hub. The dispensed wire is threaded through push rod and the implant device wire-connection feature to form a wire loop. A wire leg of the loop extends from the hub, through the tubular device push rod, to the implant device. Another wire leg extends from the implant device back to the hub. The hub may have an anchor post or fixture to which a wire end may be attached or fixed to securely anchor one leg of the wire loop. The hub also may have other securement means, for example, an adjustable line lock, to hold the other "free" leg of the wire loop as needed during the implant catheterization procedure.

During the implant procedure, the tethered implant device is moved through the catheter delivery tube using the push rod. Additional lengths of wire may be dispensed to lengthen the wire loop as the implant device is moved through and out of the catheter delivery tube if needed. The implant device remains attached or tethered to the wire loop even after it has been expelled from the catheter delivery tube and is deployed in a body cavity.

Deployed implant devices, which, for example, are not satisfactorily positioned, may be retracted into catheter delivery tube by retracting the push rod with both wire legs securely anchored in the hub. The retracted device may be redeployed or may be completely withdrawn as appropriate. Implant devices which are satisfactorily deployed may be untethered by first deactivating the line lock in the hub to free one wire end of the loop, and by then retracting the push rod so that the free end of the wire loop slides clear of the implant device wire connection feature.

Other embodiments of the tether system may have other configurations of wires (and wire securement means), which allow mechanical control over a tethered implant device.

Further features of the invention, its nature and various advantages will be more apparent from the accompanying drawings and the following detailed description.

DESCRIPTION OF THE PREFERRED EMBODIMENTS

Implant devices for filtering or otherwise modifying blood flow between an atrial appendage and its atrium may be attached to a push rod or shaft, and then be percutaneously delivered to the appendage through a catheter delivery tube inserted in a blood vessel leading to the heart.

Figure 1:
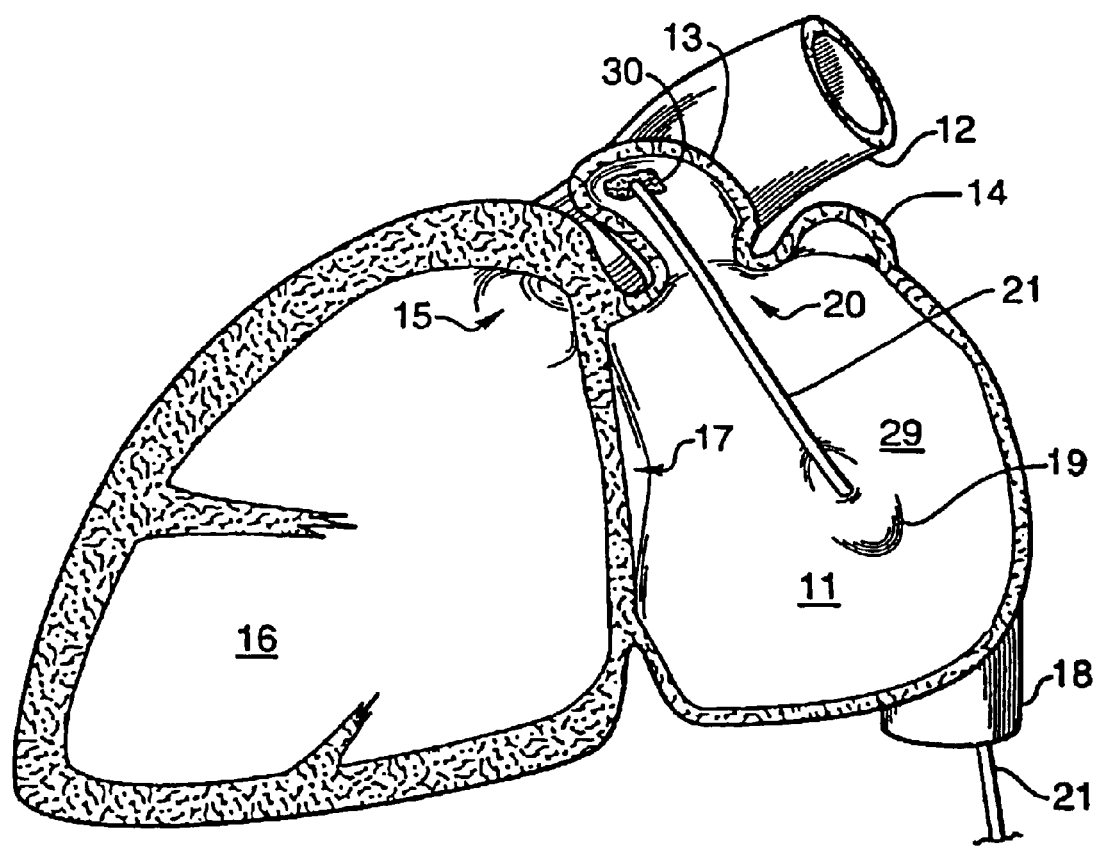
FIG. 1 is a partial cross sectional view of a heart illustrating a conventional catheter entering a left atrial appendage using a transseptal catheterization procedure.

FIG. 1 illustrates, for example, catheter 21 inserted through a femoral vein (not shown) entering the right atrium of the heart through the inferior vena cava 18, and then passing into left atrium 11 through the fossa ovalis 19 or through the septum 29 before entering the left atrial appendage 13. Alternatively (not shown in FIG. 1), catheter 21 may enter the left ventricle 16 of the heart through the aorta 12, and then pass through mitral valve 17 to reach left atrial appendage 13. An implant device (not shown) attached to catheter 21 may be used to prevent thrombus 30 or emboli generated therefrom from migrating into atrium 11.

The implant devices generally include materials having suitable properties (e.g., radio-opacity) that make it possible to monitor the in-vivo device position during and after the catheterization procedure using external imaging techniques such as radiography or fluoroscopy, echocardiography, and ultrasound. However, the circuitous path of the catheter delivery tube through the patient's vasculature across the cardiac septum may make precise placement of an implant device difficult, even when the operating physician has the benefit of using external imaging techniques to monitor the implant device position during the catheterization procedure.

The present invention provides catheterization apparatus having a device tether system in addition to the conventional features of known catheterization apparatus (e.g., previously disclosed catheterization apparatus described in U.S. Application Publication No. 20020035374A1 and U.S. patent application Ser. No. 60/351,898). A basic feature common to known catheterization apparatus is a device delivery tube, which provides a conduit or pathway for insertion of the implant device into the patient's body. Another basic feature common to known catheterization apparatus is a mechanism such as a push rod or shaft for carrying or moving the implant device through the delivery tube. It will be understood that the inventive catheterization apparatus may in general have one or more nested tubes, wires or shafts, and other features (e.g. the positioning guides that are described in U.S. Application Publication No. 20020035374A1 ). However for clarity in the description of the present invention herein, and to simplify understanding of the invention, reference will made only to the two previously mentioned basic conventional features of the inventive catheterization apparatus.

In the inventive tether system, the implant device is tethered to a length of flexible line or wire extending through a tubular push rod or shaft. The tether wire allows an operating physician to retain mechanical control over an implant device after it has been expelled from the catheter delivery tube into a body cavity. This mechanical control over post deployment devices enables the physician to recover and reposition implant devices as needed.

The tether system may be used with implant devices that have (or those that can be fitted with) a suitable wire connection feature such as an eye hole. It will also be understood that the device materials have suitable properties (e.g., radio-opacity) that make it possible to monitor the in-vivo device position during and after the catheterization procedure using external imaging techniques, for example, radiography or fluoroscopy, echocardiography, and ultrasound. Exemplary devices, which may be implanted using inventive tether system, are the reversibly expandable filter implant devices having elastic structures described in U.S. patent application Ser. No. 09/428,008, now U.S. Pat. No. 6,551,303; U.S. patent application Ser. No. 09/614,091, now U.S. Pat. No. 6,689,150; U.S. patent application Ser. No. 09/642,291, now U.S. Pat. NO. 6,652,555; U.S. U.S. patent application Ser. No. 09/697,628, now U.S. Pat. No. 6,652, 556; U.S. patent application Ser. No. 09/932,512, now published as U.S. Application Publication No. 20020022860A1; U.S. patent application Ser. No. 09/960, 749, now published as U.S. Application Publication No. 20020035374A1; and U.S. patent application Ser. No. 10/094,730, now published as U.S. Application Publication No. 20030057156A1. It will be understood that the tether system may also be used with any other type or kind of implant devices, which are amenable to delivery through catheter tubes.

In one embodiment of the invention, the tether system includes a wire-dispensing hub connected to the distal end of the tubular push rod or shaft. A flexible wire (line, cord, or string) is dispensed in the hub. The wire may be made of any suitable material, for example, metals, polymers or a combination thereof. A wire of suitable strength may be fabricated from a single strand or from multiple strands of material. The wire passes through the tubular push rod and out of the proximal end of the push rod. The dispensed wire extending out of the push rod is threaded through the implant device wire-connection feature, and passed back through the push rod to the hub. The wire loop thus formed has a wire leg extending from the hub to the implant device, and another leg extending from the implant device back to the hub. Both ends of the wire loop may be anchored or fixed securely at anchoring fixtures that are provided in the hub. The tethered device may be held firmly against (and carried on) the distal end of the push rod by suitably adjusting the length of the wire loop legs.

In a catheterization implant procedure, the push rod carrying a tethered device on its (push rod's) distal end may be used to transfer the implant device from outside the patient's body into a body cavity through a pathway formed by the catheter delivery tube. The implant device may, for example, be a self-expanding device. The device is deployed in the body cavity by pushing it through past the distal end of the catheter delivery tube. The implant device remains tethered to the wire loop even after it has been expelled from the catheter delivery tube.

External imaging techniques may be used to verify the position of the deployed device. Alternative diagnostic means, for example, electronic monitoring of the patient's physiological parameters may also be used to assess the suitability of the deployed device.

Deployed implant devices, which, for example, are not satisfactorily positioned or oriented, may be retracted into catheter delivery tube by pulling the push rod out of the catheter delivery tube. The backward motion of the push rod causes the wire loop to mechanically pull the tethered device into the catheter delivery tube. Because of its elastic structure the implant device is compressed to its compact size as it is retracted into the delivery tube. The operating physician may attempt to reposition and redeploy the retracted device in a more satisfactory position or orientation by moving the push rod forward to again expel the retracted device from the catheter delivery tube. Before attempts to redeploy the retracted device are made, the catheter delivery tube itself may be suitably repositioned or stabilized as necessary.

Alternatively, if medically appropriate, the retracted device may be retrieved from the patient's body by pulling back the push rod completely out of the catheter delivery tube.

Implant devices which are satisfactorily deployed may be untethered by first deactivating the line lock in the hub to free one wire end of the loop, and then retracting the push rod so that the free end of the wire loop slides clear of the implant device wire connection feature.

Figure 2:
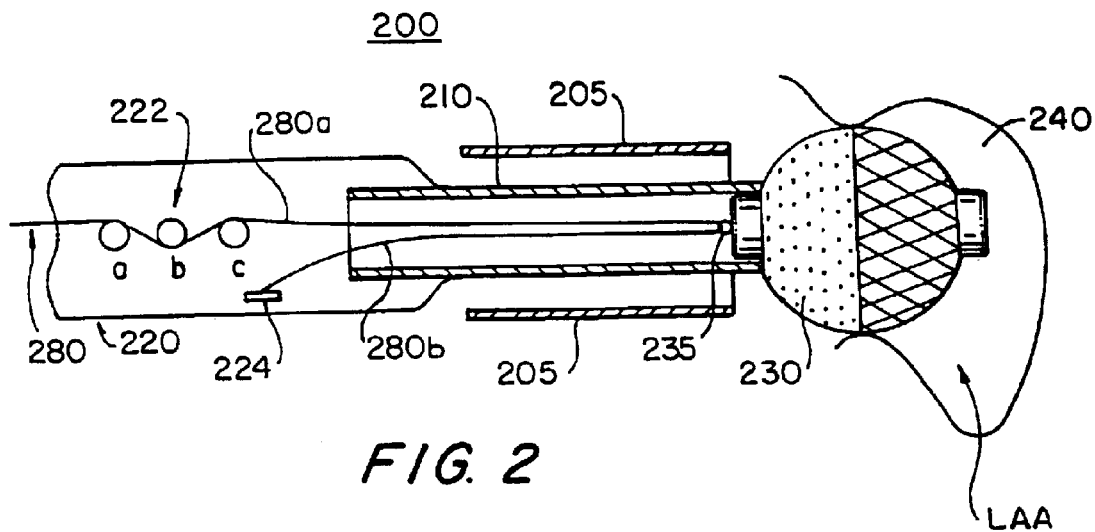
FIG. 2 is a schematic cross-sectional view of a catheterization apparatus having a device tether system, which includes a wire-dispensing hub connected to a tubular push rod that is used for moving an implant device through a catheter delivery tube in accordance with the principles of the invention. Also, an exemplary filter implant device tethered to a wire loop is shown deployed in an atrial appendage. The two wire legs of the wire loop are, respectively, shown as being anchored at an anchoring post and at a line lock mechanism in the wire-dispensing hub

FIG. 2 schematically illustrates portions of catheterization apparatus 200 having a device tether system. Catheterization apparatus 200 includes a hollow tubular shaft or push rod 210, and a catheter device delivery tube 205. Catheter delivery tube 205 and push rod 210 may be fabricated from any suitable material including metals and polymeric materials, for example, stainless steel and PTFE (e.g., Teflon). Catheter delivery tube 205 may be used to establish a percuatneous passage to a body cavity. Push rod 210 is designed to slide through catheter device delivery tube 205. Push rod 210 may be used to push or carry a compacted implant device through the device delivery tube 205 into a body cavity.

For example, FIG. 2 schematically shows delivery tube 205 forming a conduit to atrium 240. Further, FIG. 2 shows filter implant device 230, which has been expelled through device delivery tube 205, and deployed in a patient's left atrial appendage 240. Implant device 230 is provided with a eye hole 235 at its distal end.

A wire-dispensing hub 220 is mechanically connected to the proximal end of push rod 210. Hub 220 has a container-like structure, and may be fabricated from any suitable materials including metals and polymeric materials. Wire post 224 and line lock fixture 222, are disposed on an interior wall of hub 220. Line lock fixture 222 includes posts 222a, 222b, and 222c. Hub 220 may be provided with a removable access cover (not shown) to provide access to the interior of hub 220.

Implant device 230 is tethered by cable 280. Cable 280 is fixed to wire post 224, for example, by a conventional screw and washer arrangement (not shown). Cable 280 may, for example, be a polyester or nylon string. Alternatively, cable 280 may be fabricated from other suitable natural or synthetic fibers. Cable 280 extends from wire post 224 through push rod 210 lumen to implant device 230. Cable 280 passes through eye hole 235 disposed on device 230, and returns through push rod 230 lumen to hub 220. The return end of cable 280 may be wrapped around line lock posts 222a–222c, to anchor cable 280, and to thereby firmly tether implant device 230 on the distal end of push rod 210. In alternative designs of hub 220, line lock 222 may include moving levers, reels, rollers, or other mechanical structures to grip, pinch, or other wise hold and anchor the return end of cable 280. In this fashion, implant device 230 is tethered by the wire loop that is formed by cable 280 with leg 280a extending from wire post 224 to implant device 230, and leg 280b extending from the device 230 to hub 220. Implant device 230 remains tethered after it has been expelled from catheter delivery tube 205 and deployed in atrial appendage 240, as shown in FIG. 2.

Figure 3:
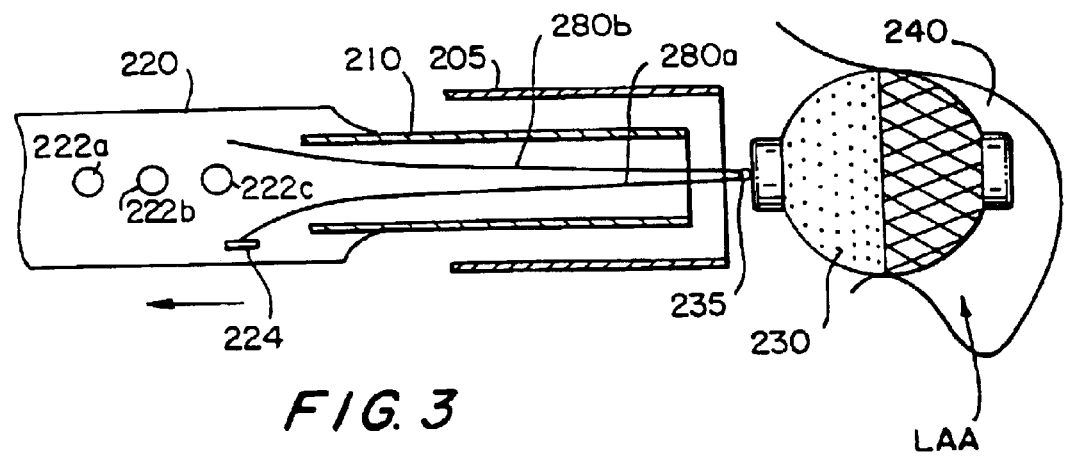
FIG. 3 is a schematic cross-sectional view of a catheterization apparatus of FIG. 2 showing the line lock mechanism deactivated to release a leg of the wire loop in preparation for untethering the deployed implant device in accordance with the principles of the invention.

To untether implanted device 230, the end of leg 280 may be unwrapped from around posts 222a, b and c, to free leg 280b from line lock 222. Push rod 210 (with connected hub 220) may then be pulled back out of catheter delivery tube 205. This back ward movement causes cable 280 to slide out of eye hole 235 and to thereby untether device 230. FIG. 3 schematically illustrates the portions of catheterization apparatus 200 shown in FIG. 2 during the untethering procedure. In FIG. 3, cable leg 280b is shown as free and unattached to line lock 222. Push rod 210 is shown as having moved back into cathter device delivery tube 205, and disengaged from device 230. Further, back ward movement of push rod 210 into catheter device delivery tube 205 would cause the free end of cable 280 to completely slide out of eye hole 235 (not shown).

It will be understood that the foregoing is only illustrative of the principles of the invention, and that various modifications can be made by those skilled in the art without departing from the scope and spirit of the invention. It will be understood that terms like "distal" and "proximal", "forward" and "backward", "front" and "rear", and other directional or orientational terms are used herein only for convenience, and that no fixed or absolute orientations are intended by the use of these terms.

What is claimed is:

1. A catheterization apparatus for implanting a device in an internal body cavity, said apparatus comprising:
   a delivery tube for establishing a conduit for passage of said device to said body cavity;
   a push rod for moving said device through said delivery tube; and
   a releasable tether attached to said device for mechanical control over said device after it has been placed in said body cavity; wherein:
   said push rod is connected to a hub disposed on an end of said push rod;
   said tether extends from said hub to said device, said device disposed on the other end of said push rod;
   said hub comprises a wire-anchoring fixture; and
   said tether comprises a wire loop with a wire end secured at said wire-anchoring fixture.

2. An apparatus for implanting a device in an atrial appendage, said apparatus comprising:
   a delivery tube for establishing a conduit through the body's vasculature, said conduit for passage of said device to said atrial appendage; and
   a shaft for transporting said device through said delivery tube; wherein:
   said shaft comprises a device tether for mechanical control over said device after said device has been placed in said body cavity;
   said shaft is connected to a hub disposed on an end of said shaft;
   said tether extends from said hub to said device, said device disposed on the other end of said shaft;
   said hub comprises a wire-anchoring fixture; and
   said tether comprises a wire loop with a wire end secured at said wire-anchoring fixture.

* * * * *